United States Patent [19]
Sheehan

[11] Patent Number: 5,601,093
[45] Date of Patent: Feb. 11, 1997

[54] SNORE-INHIBITING DEVICE

[76] Inventor: David V. Sheehan, 24791 Via San Felipe, Mission Viejo, Calif. 92692

[21] Appl. No.: 625,229

[22] Filed: Apr. 1, 1996

[51] Int. Cl.⁶ .................................................. A61F 5/56
[52] U.S. Cl. ........................... 128/848; 128/859; 128/862
[58] Field of Search ........................... 128/848, 857–862, 128/62 A; 2/2

[56] References Cited

U.S. PATENT DOCUMENTS

| | | | |
|---|---|---|---|
| 1,674,336 | 6/1928 | King | 128/848 |
| 2,521,039 | 9/1950 | Carpenter | 128/861 |
| 2,590,118 | 3/1952 | Oddo | 128/861 |
| 3,217,708 | 11/1965 | Roberts | 128/861 |
| 3,356,069 | 10/1970 | Geres | 128/136 |
| 3,692,025 | 9/1972 | Greenberg | 128/136 |
| 4,161,967 | 7/1979 | Bekey et al. | 32/17 |
| 4,169,473 | 10/1979 | Samelson | 128/136 |
| 4,173,219 | 11/1979 | Lentine | 128/136 |
| 4,196,724 | 4/1980 | Wirt et al. | 128/136 |
| 4,593,686 | 6/1986 | Lloyd et al. | 128/136 |
| 4,669,459 | 6/1987 | Spiewak et al. | 128/136 |
| 4,676,240 | 6/1987 | Gardy | 128/207 |
| 4,715,368 | 12/1987 | George | 128/136 |
| 4,901,737 | 2/1990 | Toone | 128/848 |
| 4,944,310 | 7/1990 | Sullivan | 128/848 |
| 4,986,283 | 1/1991 | Tepper | 128/859 |
| 5,003,994 | 4/1991 | Cook | 128/848 |
| 5,042,506 | 8/1991 | Liberati | 128/848 |
| 5,046,513 | 9/1991 | Murchie | 128/848 |
| 5,052,409 | 10/1991 | Tepper | 128/859 |
| 5,056,534 | 10/1991 | Wright | 128/848 |
| 5,082,007 | 1/1992 | Adell | 128/861 |
| 5,092,346 | 3/1992 | Hays | 128/848 |
| 5,117,816 | 6/1992 | Shapiro et al. | 128/200 |
| 5,154,184 | 10/1992 | Alvarez | 128/848 |
| 5,267,862 | 12/1993 | Parker | 433/215 |
| 5,284,161 | 2/1994 | Karell | 128/848 |
| 5,313,960 | 5/1994 | Tomasi | 128/848 |
| 5,316,020 | 5/1994 | Truffer | 128/848 |
| 5,328,362 | 7/1994 | Watson et al. | 433/6 |
| 5,365,945 | 11/1994 | Halstrom | 128/848 |
| 5,381,783 | 1/1995 | Hintz | 128/206 |
| 5,406,963 | 4/1995 | Adell | 128/861 |
| 5,409,017 | 4/1995 | Lowe | 128/848 |

Primary Examiner—Michael A. Brown
Attorney, Agent, or Firm—Henri J. A. Charmasson; John D. Buchaca

[57] ABSTRACT

A snore-inhibiting device shaped and dimensioned for comfortable installation within the mouth of a user includes a pair of cooperating jaw pieces configured to cap the upper and lower teeth-and-gum structures. The jaw pieces are held together slightly ajar by their integrally molded rearward portions. The small gap between the jaw pieces is enlarged in the frontal area by a rectangular slot through which a tip portion of the tongue can be pushed. The jaw pieces are allowed to separate even more slightly under the pressure of the tongue then to resiliently close back and capture the tip of the tongue, thus keeping the tongue slightly forward from the teeth line. The upper and lower jaw pieces are asymmetrical in order to favor a stable positioning of the device against the lower jaw. The device is made from a thermal plastic having a low melting point so that it may be conformed to the user's dental structure after softening by immersion into boiling water.

12 Claims, 3 Drawing Sheets

SNORE-INHIBITING DEVICE

FIELD OF THE INVENTION

This invention relates to devices for controlling snoring, and bruxism, and more particularly to device for insertion within the oral cavity of a user.

BACKGROUND OF THE INVENTION

There has been many attempts in the past to control snoring and bruxism by means of appliances which are intended to keep the jaws apart and keep the tongue in a forward position where it does not interfere with the nasal pharyngeal air passage.

One of the most advanced of such devices is disclosed in U.S. Pat. No. 4,303,227 Samuelson. In this disclosure the tongue is held into a pocket by suction forces applied over almost the entire surface of the tongue. The device completely obstructs the mouth and does not provide for alternate breathing in case of clogging of the nose.

There is a need for an oral appliance for controlling snoring and bruxism that is relatively light, small, comfortable and safe.

SUMMARY OF THE INVENTION

The principal object of this invention is to inhibit snoring and teeth-grinding by controlling the position of tongue and preventing breathing through the mouth by means of an oral appliance that can be custom-fitted to the user's oral cavity under a comfortable condition. The tip of the tongue is lightly pinched into a breathing slot but can be quickly withdrawn to clear the slot in case of nasal clogging.

DESCRIPTION OF THE PREFERRED EMBODIMENT OF THE INVENTION

Figure 1:
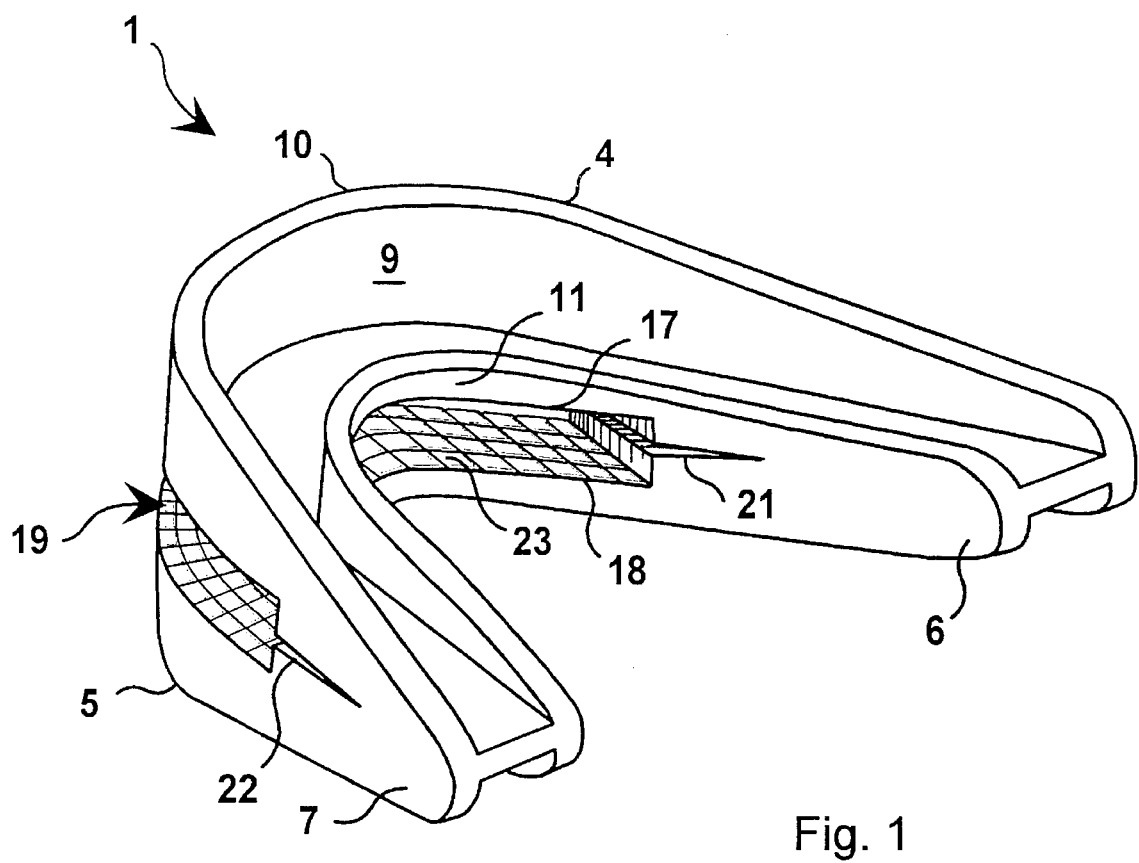
FIG. 1 is a top, left and rear isometric view of the snore-inhibiting device.
Figure 2:
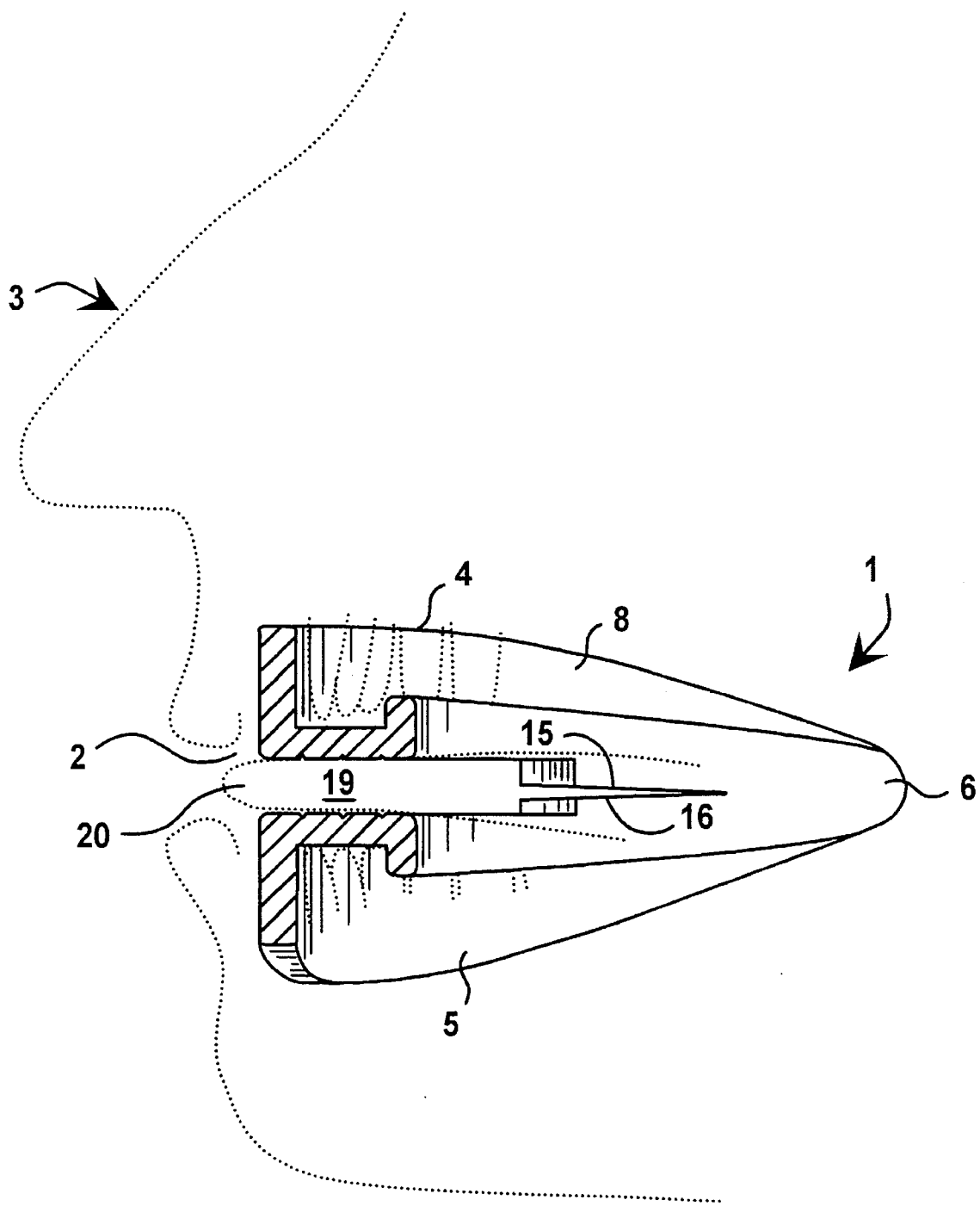
FIG. 2 is a cross-sectional of the device installed in a user's mouth.

Referring now to the drawing, there is shown a snore-inhibiting device 1 according to the invention that is specifically adapted for installation into the mouth 2 of a user 3 during nighttime. The device comprises a pair of asymmetrical, U-shaped jaw pieces 4 and 5 which are integrally joined at their rearward right and left portions 6 and 7. The jaw piece 4 is shaped and dimensioned to loosely cap the upper teeth-and-gum structure 8 of the user, and define a first channel 9 between a front wall 10 and a back wall 11. The front wall 10 is slightly higher than the back wall 11, and both walls are tapering down toward the right and left rearward portions 6 an 7.

Similarly, the bottom jaw piece 5 defines another channel 12 between a front wall 13 and a back wall 14 with both walls being of different heights and tapering down toward the rear portions 6 and 7. The front wall 13 of the bottom jaw piece is almost twice as high as the front wall 10 of the top jaw piece. The floors and of the channels 9 and 12 are substantially flat. The two jaw pieces have congruent undersurfaces 15, 16 opposite their respective channels facing each other. The frontal, median sections of each undersurface has an elongated and substantially rectangular, shallow depression 17 and 18. The depressions are lined up and oppositely facing each other, thus defining a narrow, rectangular aperture 19 shaped and dimensioned to receive a tip portion of the user's tongue 20. The non-depressed areas of the respective top and bottom jaw pieces between the slot aperture 19 and the integrally joined rearward portions 6 and 7 define a pair of slits 21 and 22.

Figure 3:
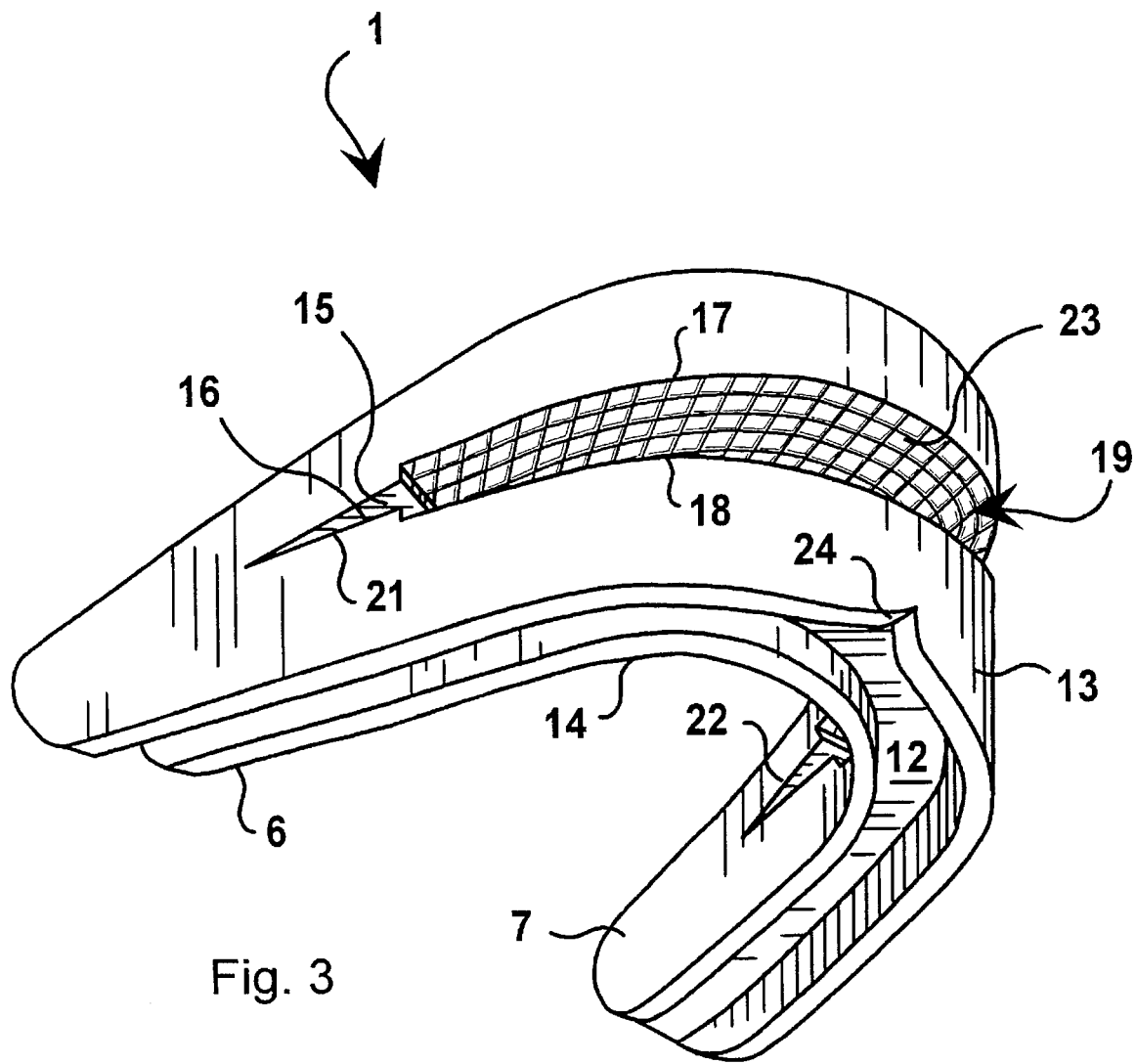
FIG. 3 is a front, bottom and right side perspective view thereof in the open condition.

The device is made from a medium density polyethylene plastic material which is resiliently stretchable to a small degree. If a larger portion of the tongue is pushed through the slot aperture 19, the top and bottom jaw pieces 4 and 5 tend to move away from one another to enlarge the slot openings 21, 22. Basically, the jaw pieces are deflected away from one another about the integrally joined rearward portions 6 and 7 acting as pivoting points. As illustrated in FIG. 3, the slits 21 and 22 open into a triangular shape as the jaw pieces separate. As the pressure exerted by the tongue is relaxed, the jaw pieces move back toward one another slightly pinching the tip of the tongue. The surface of the depressions 17 and 18 are preferably provided with dimples or serrations 23 to increase their friction coefficient. Accordingly, the user can position and immobilize his tongue in a forward position within the mouth to prevent obstruction of the nasal air passage, thus favoring breathing through the nose. The pinching force over the tip of the tongue is not so strong that, in case of clogging of the nose, the tongue cannot be easily withdrawn from the slot aperture by automatic reflex to allow breathing through the mouth.

The larger dimensions of the bottom jaw piece front wall 13 tends to position the immobilized device toward the lower half of the mouth cavity since a larger area of the device contacts the lower teeth-and-gum structure than the upper teeth-and-gum structure of the device is biased toward adhering to the lower teeth-and-gum structure.

The material used in the fabrication of the device is preferably formulated to exhibit a melting point within a range of approximately 50 to 90 degrees C. (120 to 195 degrees F.).

The device can be custom fitted to the particular geometry of the user's oral cavity by initially dipping it for about 10 seconds into water that has just ceased boiling, then for 2 or 3 seconds into water at ambient temperature to bring it to close proximity of its melting point where it can be put into the mouth and slightly reshaped by a combination of finger massaging and clamping jaw pressure.

One of the front walls 10 or 11 is provided with a indentation 24 which constitutes a tactile as well as visual indicium facilitating the proper orientation of the device even in total darkness.

The device can be made in various and different colors and sizes, and incorporate flavoring and germicidal compounds that would slowly leach out during use.

While the preferred embodiment of the invention has been described, modifications can be made and other embodiments may be devised without departing from the spirit of the invention and the scope of the appended claims.

What is claimed is:

1. A snore-inhibiting device for insertion between a user's upper and lower teeth-and-gum structures and behind said user's upper and lower lips, which comprises:

a pair of U-shaped jaw-pieces made of molded plastic material;

a first one of said pieces shaped and dimensioned to loosely cap said upper structure and a second one of said pieces being shaped and dimensioned to loosely cap said lower structure;

said pieces including co-extensively matching, opposite interfaces and integrally joined right and left rearward portions;

said interfaces having a pair of substantially symmetrical, oppositely lined-up, elongated, shallow depressions located in median, forward sections of said pieces, said depressions being spaced apart from said rearward portions; and said depressions forming an elongated slot shaped and dimensioned to allow insertion therethrough of a tip portion of said user's tongue.

2. The device of claim 1, wherein said first piece further comprises a first wall shaped and dimensioned to nest between said upper structure and said user's upper lip;

said second piece further comprises a second front wall shaped and dimensioned to nest between said lower structure and said user's lower lip; and one of said walls is higher than the other.

3. The device of claim 2, wherein said second wall is higher than said first wall.

4. The device of claim 3, defining a pair of symmetrical horizontal slits between said depression and said rearward portions;

wherein said rearward portions are made from resiliently stretchable plastic whereby said elongated slot may be enlarged by exerting separating pressure between said median, forward section of said piece by forcing additional portions of said user's tongue through said slot; and said depressions are lined-up with friction-enhancing dimples.

5. The device of claim 4, wherein said pieces are made of a thermal plastic material having a melting point within a range of approximately 50 to 90 degrees C.

6. The device of claim 2, wherein one of said front walls comprises a tactile indicia.

7. The device of claim 6, wherein said tactile indicia comprises said wall having different outlines.

8. The device of claim 1, defining a pair of symmetrical horizontal slits between said depression and said rearward portions.

9. The device of claim 1, wherein said rearward portions are made from resiliently stretchable plastic;

whereby said elongated slot may be enlarged by exerting separating pressure between said median and forward sections of said pieces by forcing additional portions of said user's tongue through said slot.

10. The device of claim 9, wherein said depressions are lined-up with friction-enhancing serrations.

11. The device of claim 1, wherein said pieces are made of a thermal plastic material having a melting point within a range of approximately 50 to 90 degrees C.

12. The device of claim 1, wherein said depressions are substantially rectangular.

* * * * *